US00PP24763P2

(12) United States Plant Patent
Tuinier

(10) Patent No.: US PP24,763 P2
(45) Date of Patent: Aug. 12, 2014

(54) ***GASTERIA* PLANT NAMED 'GREEN STAR'**

(50) Latin Name: ***Gasteria* hybrid**
Varietal Denomination: Green Star

(71) Applicant: Wander Durk Tuinier, Krimpen a/d Ijssel (NL)

(72) Inventor: Wander Durk Tuinier, Krimpen a/d Ijssel (NL)

(73) Assignee: Wander Tuinier BV, Krimpen ald Ijssel (NL)

( * ) Notice: Subject to any disclaimer, the term of this patent is extended or adjusted under 35 U.S.C. 154(b) by 50 days.

(21) Appl. No.: 13/694,638

(22) Filed: Dec. 19, 2012

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell

(57) ABSTRACT

A new cultivar of *Gasteria* plant named 'Green Star' that is characterized by an upright habit and green leaves with light green spots.

1 Drawing Sheet

Botanical classification: *Gasteria* hybrid.
Variety denomination: 'GREEN STAR'.

BACKGROUND OF THE INVENTION

The present invention relates to a new and distinct cultivar of *Gasteria* plant botanically known as *Gasteria* hybrid and hereinafter referred to by the cultivar name 'Green Star'.

'Green Star' was discovered as a naturally occurring whole plant mutation of *Gasteria* hybrid 'WT03' (not patented). 'Green Star' was discovered in July of 2010 as a single plant in a population of *Gasteria* 'WT03' plants grown from tissue culture in a greenhouse in a cultivated area of Swellendam, South Africa.

Asexual reproduction of the new cultivar 'Green Star' first occurred by tissue culture in November of 2010 in Swellendam, South Africa. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Gasteria* cultivar 'Green Star'. These traits in combination distinguish 'Green Star' as a new and distinct cultivar apart from other existing known varieties of *Gasteria*.

1. *Gasteria* 'Green Star' exhibits an upright habit.
2. *Gasteria* 'Green Star' exhibits green leaves with light green spots.

The closest comparison cultivar is the parent plant *Gasteria* 'WT03'. Green Star' is distinguishable from 'WT03' by the following characteristics:

1. *Gasteria* 'Green Star' exhibits a more upright habit than 'WT03'. The habit of 'WT03' is more spreading.
2. *Gasteria* 'Green Star' exhibits leaves that are lighter green in color than the leaves of 'WT03'.
3. *Gasteria* 'Green Star' exhibits leaves with green spots. In comparison, the leaves of 'WT03' have white spots.

4. *Gasteria* 'Green Star' exhibits a faster growth rate than 'WT03'.

BRIEF DESCRIPTION OF THE DRAWING

The accompanying photograph illustrates the distinguishing traits of *Gasteria* 'Green Star'. The plant in the photograph shows an overall view of an 18 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Gasteria* cultivar named 'Green Star'. Data was collected in Tielen, Belgium from 18 month plants grown in a glass greenhouse in 13 cm. diameter containers. The time of year was December and the temperature range was 12-22 degrees Centigrade during the day and 12-22 degrees Centigrade at night. The light level was natural light. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Green Star' has not been tested under all possible conditions and phenotypic differences may be observed with variations in environmental, climatic, and cultural conditions, however, without any variance in genotype.

Botanical classification: *Gasteria* hybrid 'Green Star'.
Annual or perennial: Perennial.
Parentage: 'Green Star' is a naturally occurring whole plant mutation of *Gasteria* 'WT03'.
Plant type: Perennial.
Vigor: Moderate.
Growth habit: Upright.
Plant shape: Rosulate succulent.
Suitable container size: 7 cm. or larger pots.
Plant height: Average 19.4 cm. in height.

Plant width: Average 25.7 cm. in width.
Low temperature tolerance: 3° Centigrade.
High temperature tolerance: 45° Centigrade.
Propagation: Tissue culture.
Growth rate: Moderate.
Crop time: Approximately 5 months.
Root system: Fine and fibrous.
Branching: No lateral branches, basal rosette of leaves grow from the base.
Foliage:
*Leaf arrangement*.—Basal rosette.
*Compound or single*.—Single.
*Number of leaves per plant*.—Average 37.
*Leaf shape*.—Lanceolate.
*Leaf apex*.—Narrow apiculate.
*Leaf base*.—Broad Cuneate.
*Leaf length*.—Average 15.5 cm.
*Leaf width*.—Average 3.6 cm. at base, average 2.7 cm. at mid-section.
*Leaf thickness*.—Average 1.0 cm. at mid-section.
*Texture*.—Glossy, moderately pustulate (both surfaces).
*Pubescence*.—Absent.
*Leaf margin*.—Finely denticulate.
*Venation pattern*.—No veins visible.
*Young leaf color* (*upper surface*).—Near 137A with base 146D and tubercles 190C.
*Young leaf color* (*lower surface*).—Near 137A with base 146D and tubercles 190D.
*Mature leaf color* (*upper surface*).—Near 147A with base near 143C and tubercles near 144B.
*Mature leaf color* (*lower surface*).—Near 147A with base near 143C and tubercles near 144B.
*Durability of foliage to stress*.—High.
Flowers: None observed to date.
Fruit and seeds: None observed to date.
Disease and pest resistance: Disease and pest resistance has not been observed.

The invention claimed is:

1. A new and distinct variety of *Gasteria* plant named 'Green Star' as described and illustrated.

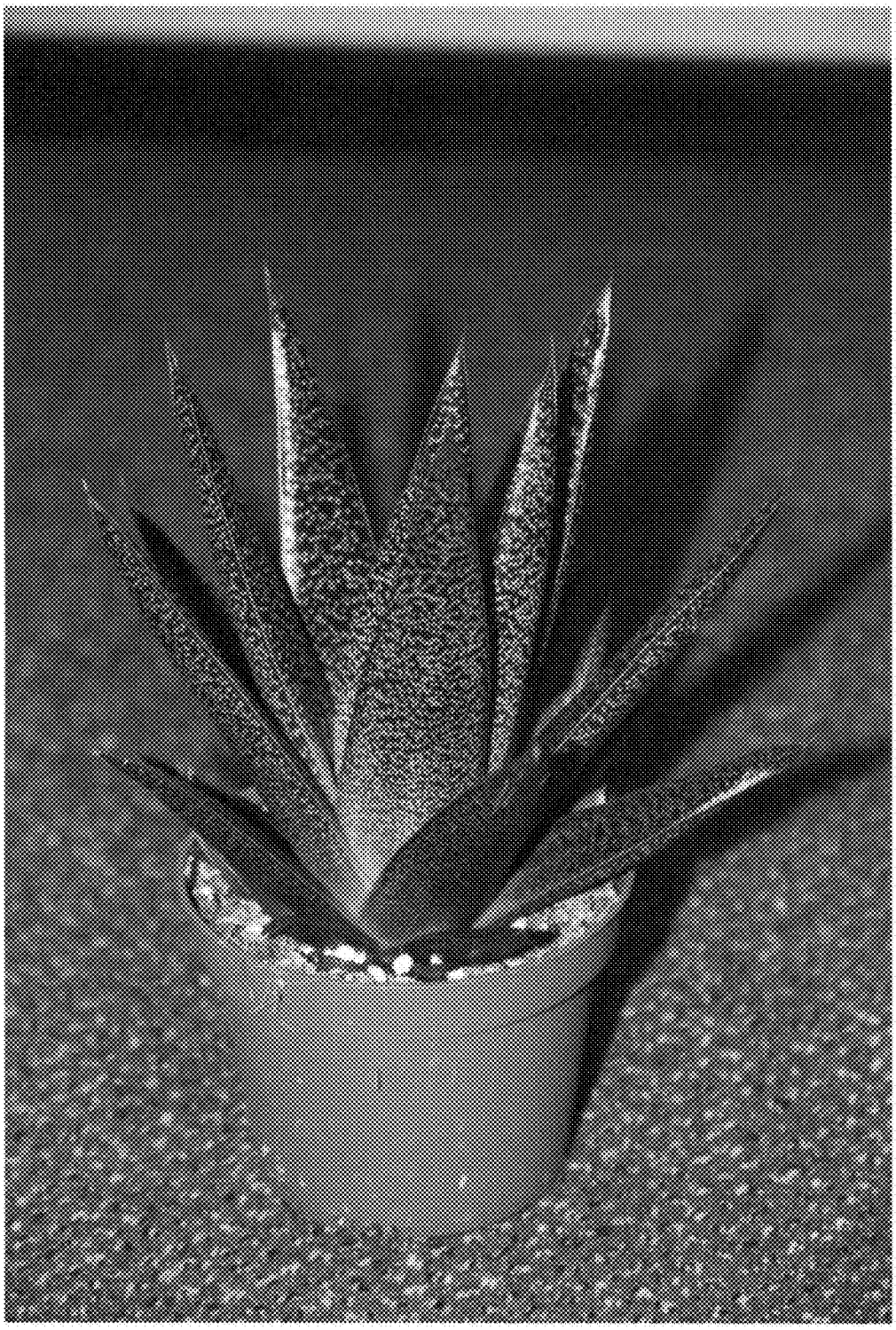

* * * * *